(12) United States Patent
Billig et al.

(10) Patent No.: US 6,452,027 B1
(45) Date of Patent: Sep. 17, 2002

(54) HEAT RECOVERY PROCEDURE

(75) Inventors: Barry Billig, Irvington; James Mann, Brooklyn, both of NY (US)

(73) Assignee: Scientific Design Company, Inc., Little Ferry, NJ (US)

( * ) Notice: Subject to any disclaimer, the term of this patent is extended or adjusted under 35 U.S.C. 154(b) by 0 days.

(21) Appl. No.: 09/949,603

(22) Filed: Sep. 10, 2001

(51) Int. Cl.⁷ .................... C07D 301/32; C07D 301/04
(52) U.S. Cl. ....................................... 549/538; 549/534
(58) Field of Search ............................... 549/538, 534

(56) References Cited

U.S. PATENT DOCUMENTS

| | | | | |
|---|---|---|---|---|
| 3,523,957 A | * | 8/1970 | Tsao | 260/348.5 |
| 4,221,727 A | * | 9/1980 | Tsang et al. | 260/348.37 |
| 4,430,312 A | * | 2/1984 | Eickmeyer | 423/223 |

* cited by examiner

Primary Examiner—Ba K. Trinh
(74) Attorney, Agent, or Firm—William C. Long

(57) ABSTRACT

The present invention provides a process treating the cycle gas from an ethylene oxide reactor to avoid heat losses in a carbonate scrubbing system as well as glycol formation in the carbonate scrubbing and catalyst contamination upon cycle gas recycle.

1 Claim, 1 Drawing Sheet

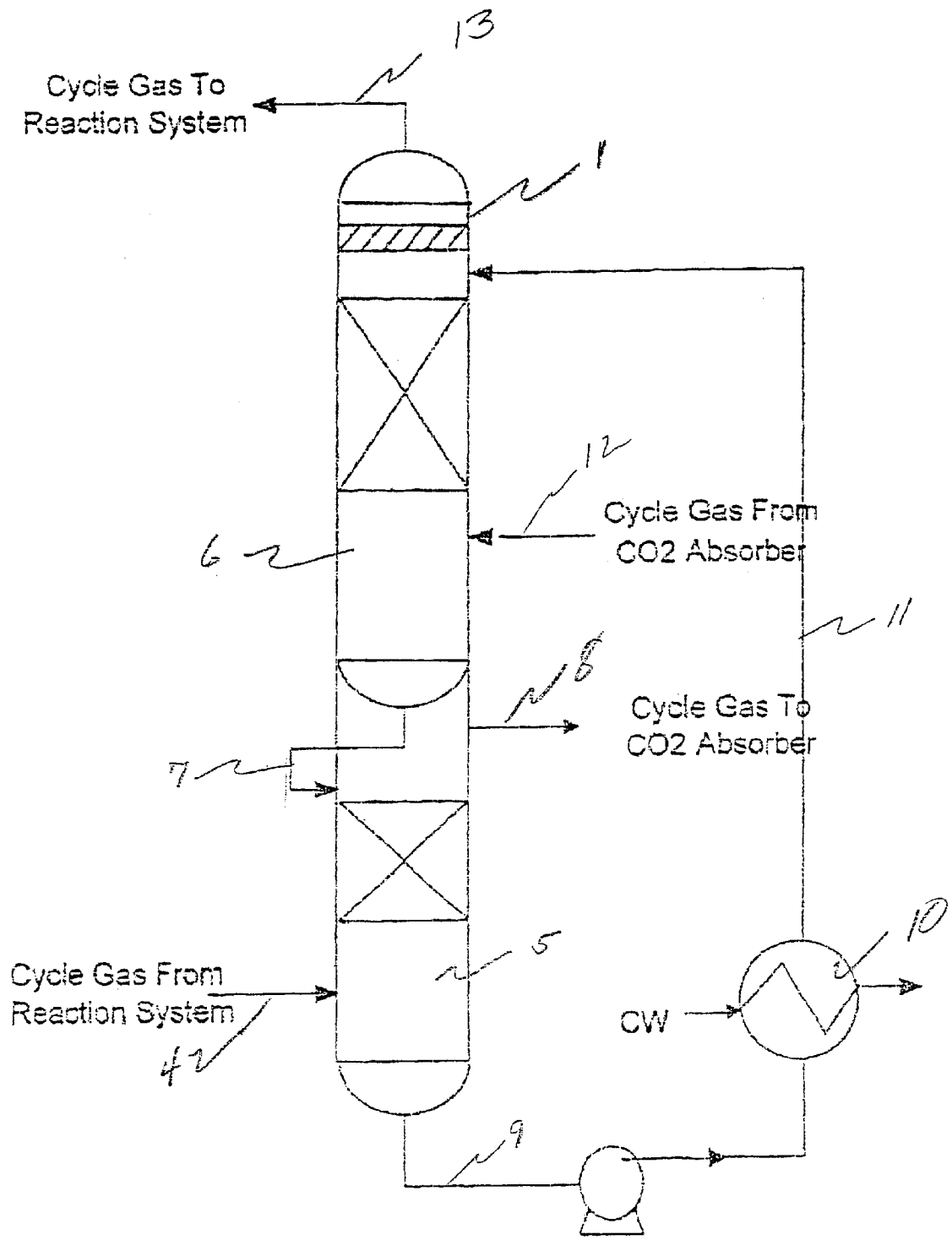

HEAT RECOVERY PROCEDURE

BACKGROUND OF THE INVENTION

1. Field of the Invention

The present invention relates to an improved heat recovery procedure in an ethylene oxide process carbon dioxide removal system.

2. Description of the Prior Art

In processes such as those where ethylene oxide is formed by the oxidation of ethylene with molecular oxygen, carbon dioxide is also produced during the oxidation. It is necessary that the carbon dioxide so produced be separated in order to prevent a build up of this product. See U.S. Pat. No. 3,523,957.

The removal of carbon dioxide from an ethylene oxide reaction system is generally done in a Hot Carbonate System (Potassium Carbonate Scrubbing System) where all or a portion of the reaction gas is sent to a $CO_2$ Absorber after the product ethylene oxide has been removed from the gas by water scrubbing in a Scrubber. The scrubbed cycle gas from the reaction system after ethylene oxide removal is normally cold as it is at Scrubber temperatures or slightly higher if it has been recompressed after scrubbing. In addition, the cycle gas is only saturated with water at the lower temperature. If this gas is sent directly to the $CO_2$ Absorber, it cools the carbonate scrubbing solution. Heat is lost from the carbonate solution in heating the cycle gas feed, as well as by the cooling due to the evaporation of water to saturate the gas at the higher operating temperature of the $CO_2$ Absorber. This heat or energy must be made up in the stripping (Regenerator) section of the $CO_2$ system where the carbonate solution is heated with steam to release the carbon dioxide to the atmosphere.

In addition to heating the Absorber feed gas, it is also necessary to cool the gas from the Absorber to remove water before the gas can be returned to the ethylene oxide reaction system since water is detrimental to the catalyst in the reaction system. Furthermore, to protect the ethylene oxide catalyst from possible carbonate contamination it is necessary to wash the gas from the Absorber with water to insure that no carbonate is carried over to the reaction section. Normally the cooling of the gas and the washing are done in two separate operations. Cooling is done in a conventional heat exchanger and washing is done in a wash tower. The heat from cooling the gas is lost to cooling water.

It is desirable to improve the economies of heat recovery in such processes since even small efficiency improvements result in major savings given the scale of world class ethylene oxide production facilities.

SUMMARY OF THE INVENTION

In accordance with the present invention, the cycle gas stream from the ethylene oxide reaction system, after ethylene oxide removal, is heated before it is passed to $CO_2$ absorption by direct contact with a circulating aqueous stream which has in turn been heated by direct contact with the cycle gas stream which is returning from the $CO_2$ absorption to the ethylene oxide reaction system. In this way, cycle gas which has been cooled during the ethylene oxide scrubbing separation is heated and saturated with water at the higher temperature before passing to the hot carbonate absorption system. Undesirable cooling and heat loss from the carbonate system is minimized. After $CO_2$ removal, the cycle gas prior to return to the reaction system is cooled and scrubbed of residual carbonate, and the water content lowered, by contact with the cooled circulating water stream used to heat the cycle gas. The heat from the gas returning from the $CO_2$ absorber is efficiently transferred to cycle gas passing to $CO_2$ absorption.

BRIEF DESCRIPTION OF THE DRAWINGS

The attached drawing is a schemmatic representation of a practice of the invention.

DETAILED DESCRIPTION

Not shown in the drawing is the conventional production of ethylene oxide by molecular oxygen oxidation of ethylene or the conventional water scrubbing of product ethylene oxide. These are well known procedures which are widely practiced commercially.

Referring to the drawing, presaturator 1 is provided which has upper section 6 and lower section 5, each section being adapted for intimate vapor-liquid contact. Preferably each section is provided with inert packing to facilitate the vapor-liquid contact.

Cycle gas from the ethylene oxide reactor after ethylene oxide removal by scrubbing is introduced via line 4 into lower section 5 of presaturator 1. The cycle gas introduced via line 4 from the scrubbing operation is relatively cool, illustratively 32 to 50° C. In lower section 5, the cycle gas is intimately contacted with a heated aqueous stream from upper section 6 which is introduced into section 5 via line 7. The aqueous stream introduced via line 7 is illustratively at 70 to 85° C.

As a result of the contact in section 5 the cycle gas stream is heated to about 65 to 80° C. and saturated with water at that temperature. This heated cycle gas passes via line 8 to a conventional hot carbonate absorption step, where $CO_2$, formed during ethylene oxidation, is removed. Because the cycle gas is heated in the presaturator before passing to the hot carbonate absorber, cooling of the hot carbonate stream is minimized.

The aqueous contact stream is passed via line 9 from the lower section 5 of presaturator 1 to cooler 10 wherein the stream is further cooled, illustratively to 40 to 45° C. The cooled aqueous stream passes via line 11 to the upper section 6 of presaturator 1 wherein the cooled aqueous stream intimately contacts and cools the cycle gas stream returning via line 12 from the hot carbonate absorption.

In section 6, the cycle gas from the absorber is both cooled and scrubbed of contained carbonate, which would deleteriously affect the ethylene oxide catalyst were it to be returned to the ethylene oxide reactor.

From section 6 the aqueous contact stream, now heated illustratively to 65 to 85° C. passes via line 7 to lower section 5 wherein as above described it preheats the cycle gas prior to passage of the cycle gas to the hot carbonate absorber.

Cooled cycle gas which is illustratively at a temperature of 45 to 48° C., containing negligible carbonate and having a lowered water content as compared to the stream in line 12, passes via line 13 as recycle to the ethylene oxide reaction system.

Practice of the invention, as described in the drawing, has a number of significant advantages over conventional systems. Besides recovery of heat from the cycle gas from the $CO_2$ absorber, the wash water rate can be set very high to give an improved wash compared to a conventional free standing wash system. In addition the pressure drop of the cycle gas is lower than when an exchanger is used. This helps reduce the power requirements in the ethylene oxide reaction system.

A secondary benefit, which is very important for a hot carbonate system, is the reduction of residual ethylene oxide in the cycle gas feed to the $CO_2$ absorber. Typically when the ethylene oxide product is scrubbed from the cycle gas some small quantity of ethylene oxide remains in the gas. When this gas is sent to the hot carbonate system the residual ethylene oxide contained therein is converted to glycol, which builds up in the stream until it is removed in the $CO_2$ vent. The glycol becomes a pollution problem and provisions often are required to remove it. The reduction of residual ethylene oxide in the absorber feed is of particular importance for maintenance of a low level of $CO_2$ in the ethylene oxide reaction system, as the quantity of cycle gas fed to the absorber is increased. For example, at 7 vol % $CO_2$ in the ethylene oxide reaction gas only about 20% of the cycle gas is fed to the absorber. However, when it is required to maintain 1 vol % $CO_2$ all of the cycle gas is fed to the absorber, increasing the potential glycol made by a factor of 5 times if the residual ethylene oxide in the absorber feed is not reduced.

The following example illustrates the invention with reference to the attached FIGURE.

EXAMPLE

In a 600,000 MT/YR ethylene oxide plant the stream 4 cycle gas from the reaction system after ethylene oxide scrubbing is 13,300 kg-moles/hr for a low $CO_2$ design with a typical composition of 2.2 vol % $CO_2$ and a water content of 0.39 vol %. The residual ethylene oxide content is 30 vol ppm. The temperature is 41° C. and the pressure is 20.0 bars. The water circulation stream 7 would be approximately 70,400 kg-moles/hr at a temperature of 43° C. The circulation water stream after it leaves the gas cooling section 6 has been heated to 79.3° C. This water is contacted with the cycle gas ie. packed section 5 of presaturator 1. The gas is heated to 77° C. and the liquid is cooled to 57° C. Approximately 28.2 million kcals are transferred from the liquid to the gas. The gas temperature is raised to 77° C. and the water content is raised to 2.12 vol. %. The ethylene oxide content of the gas feed to the $CO_2$ absorber is reduced by 60%.

The water from the gas heating section 5 is pumped and cooled in heat exchanger 10 to 43° C. before being returned to the top of the gas cooling section 6. In the upper cooling section the water is contracted with the gas from the $CO_2$ absorber again in a packed section 6. The gas returning from the $CO_2$ absorber via line 12 is at 98° C. and has a water content of 3.6 vol %. The gas is cooled to 45° C. by the circulating water in section 6 and its moisture content is reduced to 0.49 vol %. In addition to the cooling, the cycle gas picks up ethylene oxide which was dissolved in the water in lower section 5 raising the ethylene oxide content from zero in stream 12 coming back from the absorber to 17.5 vol. ppm in stream 13. Thus is recovered 60% of the ethylene oxide that was in the original feed gas.

The cycle gas returning to the reaction system via line 13 has its $CO_2$ content reduced in the absorber, from 2.1 vol % in the original feed gas to 1.0 vol %. The pressure of the returning gas is 19.7 bars which represents a pressure drop for the total system of only 0.3 bars of which 0.2 bars is in the presaturator 1. This compares to about 0.6 bars when a conventional heat exchanger is used.

In this example the following objectives have been accomplished according to the invention about 62% of the available heat in the gas stream 12 from the $CO_2$ absorber is recovered and transferred to the cycle gas feed to the $CO_2$ absorber. The $CO_2$ absorber return gas has been washed and cooled to reduce its moisture content. The residual ethylene oxide content of the feed gas to the $CO_2$ absorber has been reduced by 60%. The objectives are accomplished with a lower pressure drop than a conventional design.

In the context of a world class ethylene oxide facility, extremely significant savings are achieved.

It will be apparent that sections 5 and 6, which are shown in the same presaturator in the drawing, can also be in separate vessels or combined with other vessels such as the $CO_2$ Absorber. The concept is the same and sections 5 and 6 operate in the same fashion as described.

We claim:

1. In a process for the production of ethylene oxide wherein ethylene oxide is scrubbed from a cycle gas stream, the scrubbed cycle gas stream is contacted with a hot carbonate absorber solution to absorb $CO_2$, and the cycle gas stream after $CO_2$ absorption is recycled to ethylene oxide production, the improvement which comprises contacting the scrubbed cycle gas stream from ethylene oxide removal in a first contact step with a heated aqueous liquid in order to heat the cycle gas stream and scrub contained ethylene oxide therefrom and cool the said aqueous liquid, passing the heated cycle gas to a hot carbonate absorption step to remove $CO_2$, cooling the cycle gas from the carbonate absorption and removing carbonate therefrom by contact in a second contact step with the said aqueous liquid from the first contact step after cooling said aqueous liquid, passing the aqueous liquid from the second contact step to the first contact step and passing cooled cycle gas from the second contact step to the ethylene oxide reaction.

\* \* \* \* \*